United States Patent
Tokuyama

(10) Patent No.: US 8,287,925 B2
(45) Date of Patent: Oct. 16, 2012

(54) CELL-PROLIFERATING AGENT OR TISSUE-REPAIRING AGENT DERIVED FROM WHITE RICE

(76) Inventor: Takahito Tokuyama, Kagawa (JP)

( * ) Notice: Subject to any disclaimer, the term of this patent is extended or adjusted under 35 U.S.C. 154(b) by 787 days.

(21) Appl. No.: 11/988,336

(22) PCT Filed: Jul. 4, 2006

(86) PCT No.: PCT/JP2006/313291
§ 371 (c)(1),
(2), (4) Date: Jan. 16, 2009

(87) PCT Pub. No.: WO2007/004637
PCT Pub. Date: Jan. 11, 2007

(65) Prior Publication Data
US 2009/0285918 A1    Nov. 19, 2009

(30) Foreign Application Priority Data
Jul. 4, 2005  (JP) .................................. 2005-195473

(51) Int. Cl.
A61K 36/00 (2006.01)
(52) U.S. Cl. ........................................ 424/750; 424/725
(58) Field of Classification Search ........................ None
See application file for complete search history.

(56) References Cited

U.S. PATENT DOCUMENTS
3,097,145 A * 7/1963 Shimazono et al. .......... 435/223

FOREIGN PATENT DOCUMENTS

| JP | 59-137422 | | 8/1984 |
| JP | 61-143323 | | 7/1986 |
| JP | 7-10767 | | 1/1995 |
| JP | 07-010767 A | * | 1/1995 |
| JP | 2004-99503 | | 4/2004 |
| JP | 2004-182610 | | 7/2004 |
| WO | WO-2005/065700 | | 7/2005 |

OTHER PUBLICATIONS

2003 "Influence to cell protection ability and damage repairing ability of rat gastric mucous membrane epidermal cell affected by rice fermentation extract." Tamotsu Matsuhashi et al. Nippon Shoka Kyushu Gakkai Sokai Program ni Oyobosu Eikyo. vol. 34 p. 123.

* cited by examiner

Primary Examiner — Patricia Leith
(74) Attorney, Agent, or Firm — Jordan and Hamburg LLP

(57) ABSTRACT

Provided are more effective cell-proliferating and tissue-repairing agents derived from rice containing, as an active ingredient, an internal solution produced by the dialysis of a water-treated product of a raw rice material essentially including a white rice fraction with an 8K dialysis membrane.

1 Claim, 2 Drawing Sheets

[Fig. 1]
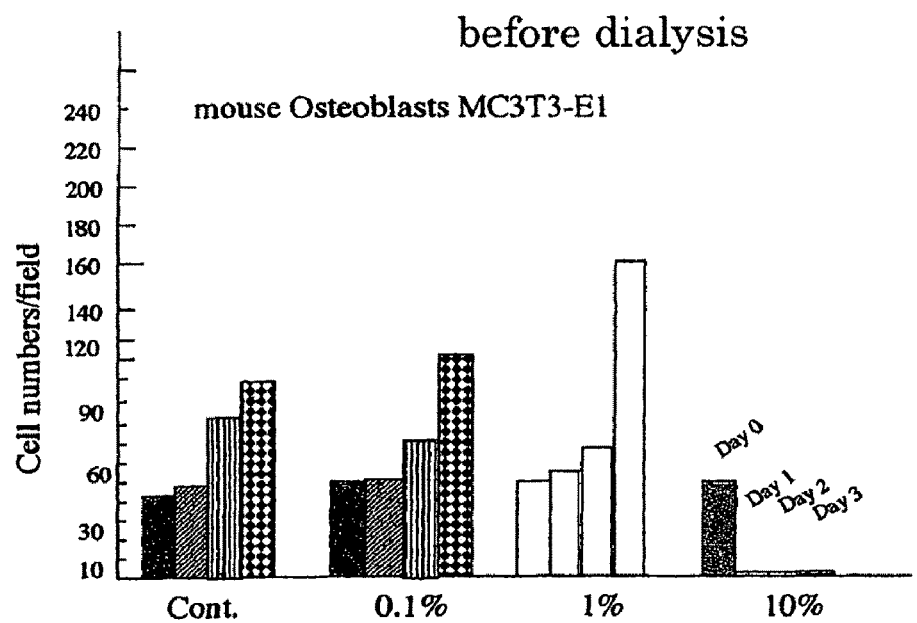
[Fig. 2]
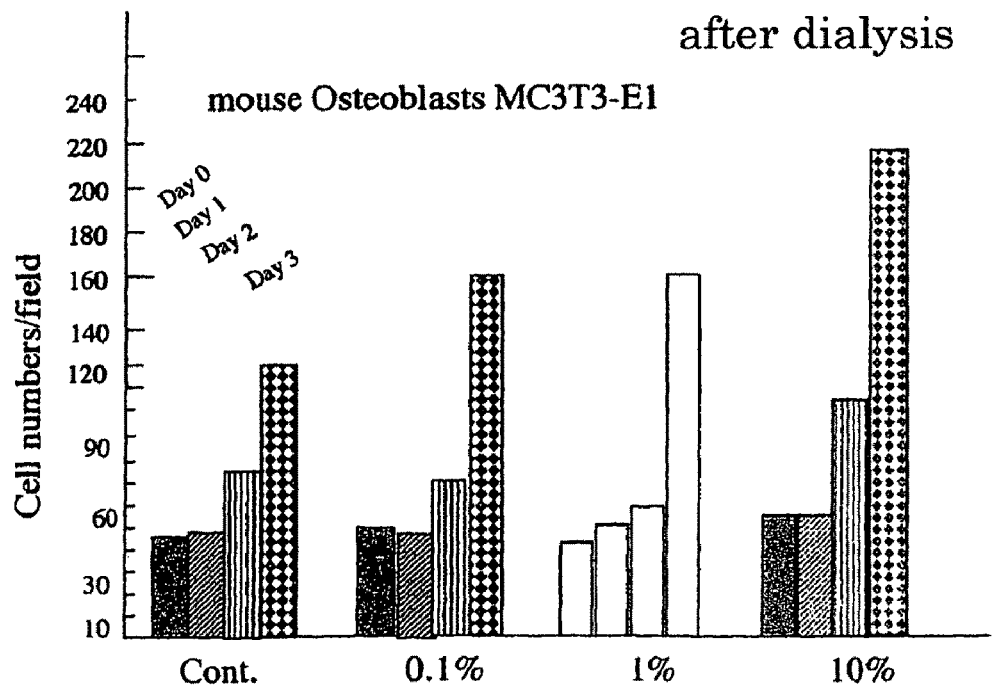

[Fig. 3]
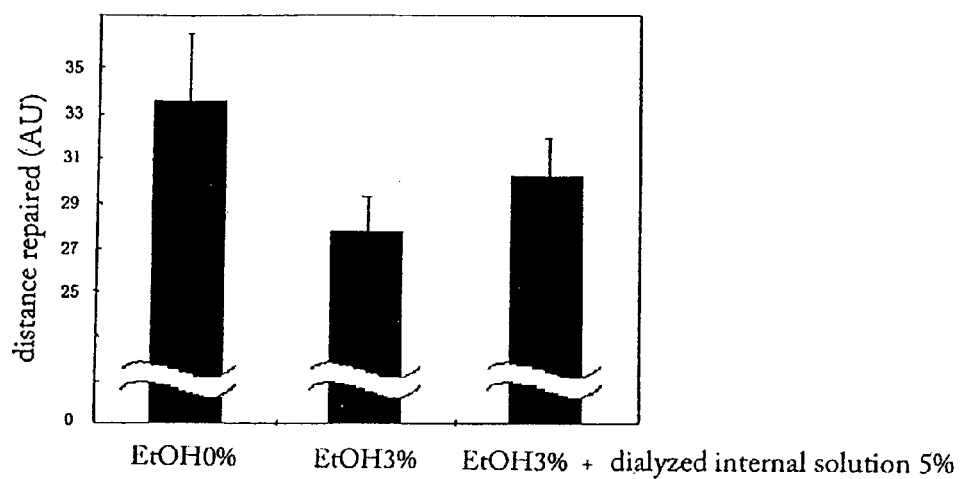

CELL-PROLIFERATING AGENT OR TISSUE-REPAIRING AGENT DERIVED FROM WHITE RICE

TECHNICAL FIELD

The present invention relates to cell-proliferating and tissue-repairing agents containing an ingredient derived from white rice as an active ingredient, useful, for example, in the field of tissue regeneration.

BACKGROUND ART

Currently, techniques capable of proliferating cells, such as differentiated cells and stem cells in large scale in a short period of time are needed especially in the field of regenerative medicine. In regenerative medicine, procedures are adopted, in which autologous cells (in particular, stem cells) collected mainly from patients are cultured, proliferated and/or differentiated extracorporeally and the regenerated tissues are transplanted. In so doing, in order to minimize aggravation of patients' diseases, various cells such as differentiated cells and stem cells must be proliferated in vitro or otherwise in large quantity in a short period of time. In addition, when tissues are damaged, together with the proliferation of cells involved in such tissues in large quantity in a short period of time, the migration activities of such cells must be increased, in order to repair the tissues efficiently.

On the other hand, the present inventors, with a view that fauna and flora go well with each other, have been conducting researches focused on white rice, which is our principal foodstuff and has the highest safety. Incidentally, during such researches, the inventors have found that water extracts and the like of the material have excellent cell-proliferating and tissue-repairing functions and already filed a patent application concerning the subject matter (Patent Reference 1, PCT/JP2005/000261).

SUMMARY OF THE INVENTION

It is the object of the present invention to further improve the water extracts and the like derived from white rice described above to provide more effective cell-proliferating and tissue repairing agents.

As a result of making modifications from a variety of perspectives for raw materials and/or process conditions, the present inventors have found that the water extracts and the like derived from white rice described above contain substances which inhibit cell-proliferating and tissue-repairing functions and that such substances can be eliminated by making predetermined treatment to the water extracts and the like derived from white rice described above, to successfully accomplish the invention in its various embodiments.

In a first embodiment, the present invention relates to a cell-proliferating agent containing, as an active ingredient, an internal solution produced by the dialysis of a water-treated product of a raw rice material essentially including a white rice fraction with an 8K dialysis membrane.

In a second embodiment, the present invention relates to the cell-proliferating agent of the first embodiment wherein the raw rice material is white rice, brown rice, sprouted rice, white bran and a combination of one or more thereof.

In a third embodiment, the present invention relates to the cell-proliferating agent according to the first and second embodiments wherein the water-treated product is a water extract of the raw rice material.

In a fourth embodiment, the present invention relates to the cell-proliferating agent according to any one of the first through third embodiments wherein the water-treated product is a saccharified product of the raw rice material or the water extract.

In a fifth and further embodiment, the present invention relates to the cell-proliferating agent according to any one of the first through fourth embodiments wherein the water-treated product is an alcohol-fermented product or organic acid-fermented product of the raw rice material, the water extract or the saccharified product.

In a sixth embodiment, the present invention relates to a tissue-repairing agent containing, as an active ingredient, an internal solution produced by the dialysis of a water-treated product of a raw rice material essentially including a white rice fraction with an 8K dialysis membrane.

In a seventh embodiment, the present invention relates to the tissue-repairing agent according to the sixth embodiment wherein the raw rice material is white rice, brown rice, sprouted rice, white bran and a combination of one or more thereof.

In an eighth and further embodiment, the present invention relates to the tissue-repairing agent according to either of the seventh and eighth embodiments wherein the water-treated product is a water extract of the raw rice material.

In a ninth embodiment, the present invention relates to the tissue-repairing agent according to any one of the sixth through eighth embodiments wherein the water-treated product is a saccharified product of the raw rice material or the water extract.

In a tenth and still further embodiment, the present invention relates to the tissue-repairing agent according to any one of the sixth through ninth embodiments wherein the water-treated product is an alcohol-fermented product or organic acid-fermented product of the raw rice material, the water extract or the saccharified product.

Terms as used herein will now be defined with respect to their meanings. For convenience, some of the terms will be defined with respect to their meanings in DETAILED DESCRIPTION OF THE INVENTION. First, "cell" in "cell-proliferating agent" is a concept which encompasses both differentiated cells and stem cells. Here, "differentiated cells" refer to cells specialized in function and morphology (for example, muscle cells, nerve cells and so on) which, unlike stem cells, have little or no multipotency. Examples of differentiated cells include epidermal cells, pancreatic parenchymal cells, pancreatic duct cells, hepatic cells, blood cells, myocardial cells, musculoskeletal cells, osteoblasts, musculoskeletal blast cells, nerve cells, vascular endothelial cells, chromocytes, smooth muscle cells, fat cells, bone cells and cartilage cells. "Stem cells" refer to cells having autonomously replicating ability and multipotency, which are capable of regeneration when tissues are damaged, including both embryonic stem (ES) cells and tissue stem cells (tissue-specific stems cells and somatic stem cells). Here, "embryonic stem cells" refer to pluripotent stem cells derived from early embryos. Also, "tissue stem cells" refer to cells, unlike embryonic stem cells, that are limited in the direction of differentiation. They are found at specific locations in the tissues and have undifferentiated intracellular structures and can be classified into ectodermal (found mainly in the brains; nerve stem cells), mesodermal (found mainly in the bone marrows; vascular stem cells, hematopoietic stem cells and mesenchymal stem cells) and endodermal (found mainly in the internal organs; hepatic stem cells and pancreatic stem cells) stem cells. In addition, the cells may be derived from any organism (for example, vertebrates and invertebrates).

However, cells derived from vertebrates are preferable, those derived from mammals (for example, primates and rodents) are more preferable, those derived from primates are particularly preferable and those derived from human are most preferable.

"Tissue" in "tissue-repairing agent" refers to a group of cells, having certain similar actions within the group, examples of which include part of internal organs. Here, "organ" refers to a structure having a single independent morphology in which one or more tissues are combined to provide certain functions. For example, the stomach, liver, intestines, pancreas, lungs, tracheae, nose, heart, arteries, veins, lymph nodes (lymphatic system), thymus, ovary, eyes, ears, tongue and skin can be mentioned. Further, the tissues may be derived from any organism (for example, vertebrates and invertebrates). However, tissues derived from vertebrates are preferable, those derived from mammals (for example, primates and rodents) are more preferable, those derived from primates are particularly preferable and those derived from human are most preferable.

"Water-treated product" refers to a processed product made from raw rice materials using water, examples of which include water extracts of raw rice materials, saccharified products under the presence of water (for example, raw rice materials saccharified with addition of water and saccharified water extracts of raw rice materials), fermented products under the presence of water (for example, raw rice materials fermented with addition of water, fermented products of water extracts of raw rice materials and fermented products of saccharified water extracts of raw rice materials). Here, "water" refers to an aqueous medium essentially comprising water and includes water and mixtures of water and an alcohol.

"Water extract" refers to physical treatment (for example, squeezing or pressing and heating), chemical treatment (for example, acid and alkali treatment) and biological (biochemical) treatment (for example, koji mold, microbial treatment and enzymatic treatment) carried out alone or in combination. For example, raw rice materials with water added, raw rice materials treated with an acid or alkali, water-added raw rice materials acted upon by an enzyme or koji mold (before or simultaneously with extraction) or those made by such treatment with or without heating may be mentioned. As described above, since "water extract" encompasses those acted upon by a saccharifying enzyme or koji mold, it includes saccharified products. Such saccharified products are, however, a different concept from the "saccharified products" described above.

"Containing, as an active ingredient" means that it contains a relevant ingredient to such an extent that cell-proliferating or tissue-repairing effects may be provided, including not only the case where the ingredient composes part of a cell-proliferating or tissue-repairing agent but as well the case where the ingredient compose the cell-proliferating or tissue-repairing agent in its entirety.

"8K dialysis membrane" in "internal solution produced by the dialysis with an 8K dialysis membrane" refers to Spectra Biotech Membrane/Por 2.1, MWCO 8000, 00016 mm, manufactured by Spectra/Por. The present invention is not limited to embodiments in which the mentioned dialysis membrane is used and includes other embodiments in which other dialysis membranes are used or other procedures are used for treatment instead of dialysis, as long as the active ingredient that is obtained when the mentioned dialysis membrane is used is contained. Molecular weights herein are on the basis of the pore size of dialysis membranes.

"Organic acid fermentation" refers to acetic acid fermentation and lactic acid fermentation, for example.

According to the present invention, since the substances which inhibit cell proliferation and tissue repair are mostly eliminated, cell-proliferating and tissue-repairing effects several times greater (refer to EXAMPLES) in comparison with conventional those of water extracts and the like derived from rice may be provided. Further, since white rice as a principal foodstuff is the raw material, biosafety is extremely high. Therefore, not only in vitro applications in which cells are cultured and returned into a body are possible, but in vivo applications in which administration is made directly into a body (for example, oral or transcutaneous administration) are possible as well. In addition, it is extremely significant that a new use of rice has been found and that an increase in its consumption can be expected through image improvement of rice, at the present time when rice is reportedly overproduced.

BRIEF DESCRIPTION OF THE DRAWINGS

FIG. 1 shows the results of cell proliferation experiment using predialysis samples (Test Example 1);

FIG. 2 shows the results of cell proliferation experiment using postdialysis samples (Test Example 1); and FIG. 3 shows the results of ethanol-induced damage repair experiment (Test Example 2).

DETAILED DESCRIPTION OF THE INVENTION

"Raw rice material essentially including a white rice fraction" according to the present invention is not particularly limited as long as it contains at least a fraction of white rice (white bran fraction) and is a concept encompassing not only white rice, brown rice and sprouted rice, but white bran alone and a blend of white bran and red bran as well. Here, white rice and brown rice refer to brown rice and white rice of nonglutinious rice, sticky rice (mochigome) and the like, regardless of the variety such as japonica or indica. Also, white bran refers to a white bran fraction of rice produced at or below 92% of polishing and any fraction within this range may be used as a raw material (for example, all white bran produced at or below 92% of polishing, white bran produced only at 92 to 80%, white bran produced at or below 60%). Red bran refers to a fraction of rice produced at or above 92% of polishing. Since the active ingredient is stable against heat and light, the raw material described above may be subjected to treatment, such as immersion, steaming, roasting (of any kind, such as sand roasting, grille roasting and hot air roasting), steam roasting, surface modification such as freeze-drying, optical modification such as irradiation with ultraviolet radiation, pressurized roasting such as pat rice as well as frying.

When sprouted rice is produced, rice with embryo buds is immersed in water or sprayed with water to sprout them. Temperatures for sprouting are from 5 to 70° C. Once sprouted, however, temperature or duration does not matter. If water is in danger of putrefaction during sprouting, the water should preferably be replaced or some measures for antisepsis should preferably be taken, in order to prevent such septic action. Here, sprouting refers to the whole process from immediately before sprouting to completion of sprouting. The sprouted rice is thoroughly rinsed before use. It may be dried at the same time.

For water treatment (for example, water extraction), the raw rice material should preferably be granular or powdery. If it is not granular or powdery, treatment time should be longer. Embodiments of water treatment will be described below.

First, water extract will be described in detail. When raw rice material is water-extracted, extraction can efficiently be made at elevated temperatures, but can also be made sufficiently at lower temperatures. When the temperatures are low at 40° C. or below, however, it is desirable that pH is rendered acidic or alkaline or that a preservative or alcohol is added, so that the raw rice material may not putrefy. Durations for extraction may be longer or shorter as long as the active ingredient can be extracted, and may be determined depending on the extraction temperature. Also, the water extraction may be carried out under pressure or at normal pressure or may be carried out under reduced pressure. For water extraction, the biggest concern is gelatinization. Once gelatinization occurs, not only efficiency in extraction is impaired, but practical operations will extremely be difficult as well. In order to prevent it from occurring, amylase may be added for reaction or hydrochloric acid or the like may be added for acidification to degrade starch. By these measures, the concern may well be solved, with no practical problems at all.

Since the active ingredients in the water extract may be stable in acid and alkali, acid decomposition extraction or alkali decomposition extraction can also effectively be carried out. In that case, neutralization and desalting are carried out as necessary. In addition, the raw rice material may be enzymatically degraded or koji mold may be worked. Enzymatic degradation as used here refers to working one or more of enzymes acting upon rice, such as starch-degrading enzymes (liquefying enzymes and saccharifying enzymes), protein-degrading enzymes, fat-degrading enzymes, fiber-degrading enzymes, lignin-degrading enzymes and pectin-degrading enzymes. For example, starch-degrading enzymes (liquefying enzymes and/or saccharifying enzymes) or koji mold may be worked during extraction for saccharification. Also, the type of koji mold or the variety of rice does not matter. For extraction, such enzymes and koji mold may be worked before or simultaneously with extraction.

Next, saccharified products will be described. The saccharified products are made by working starch-degrading enzymes or koji mold on the raw rice materials under the presence of water or working the starch-degrading enzymes or koji mold on the extract. Here, the starch-degrading enzymes refer to liquefying enzymes and/or saccharifying enzymes. Again, the type of koji mold or the variety of rice does not matter. Also, working of the starch-degrading enzymes on the extract includes one wherein the extract itself is already saccharified in part (for example, wherein a liquefying enzyme is used during the extraction step) and this means that such a partially saccharified product is further saccharified.

Next, fermented products will be described in detail. The fermented products are made by fermenting the raw rice materials under the presence of water, fermenting the water extract or fermenting the saccharified product. Here, the fermentation refers to alcoholic fermentation or organic acid fermentation (such as lactic acid fermentation). The fermentation may be carried out not only after the treatment described above (water extraction treatment and saccharification treatment) but also simultaneously with such treatment. Fermentation simultaneous with extraction treatment corresponds to "fermenting a raw rice material under the presence of water," and fermentation simultaneous with saccharification corresponds to "fermenting the water extract." Here, for alcohol fermentation to provide greater cell-proliferating or tissue-repairing effects, sequential saccharification and fermentation is more preferable to simultaneous saccharification and fermentation as a process for producing sake. Also, sugar may be eliminated by aerated fermentation using yeasts, alcohol precipitation or the like. Further, when organic acid fermentation is carried out, the cell-proliferating or tissue-repairing effects will further be increased. In particular, lactic acid fermentation is preferable.

The water extract obtained as described above is treated with an 8K dialysis membrane. The internal solution contains cell-proliferating and tissue-repairing ingredients of 8K or more, while the external solution contains cell-proliferating and tissue-repairing blocking ingredients at or below that molecular weight. The cell-proliferating and tissue-repairing ingredients have a molecular weight of preferably 10K or more or, more preferably, 12K or more.

The cell-proliferating and tissue-repairing agents according to the present invention are administered to subjects (cells, tissues, internal organs or individuals) as they are, as concentrated or diluted or in admixture with other ingredients. Here, when cells are extracted from a human body and proliferated before being returned to the human body, such cells may be syngeneic (autologous), allogeneic (non-autologous) or xenogeneic. When rejection is assumed, autologous cells are preferred.

EXAMPLES

Production Example 1

White rice was milled in a grinder to obtain 1 kg of white rice grind. 5 g of a liquefying enzyme and 3 L of water were added to the grind, which was left to stand at 60° C. for four hours. Subsequently, it was heated to an elevated temperature and, after cooling, solid-liquid separation was carried out using a filter to obtain 2.5 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 2

White rice was milled in a grinder to obtain 1 kg of white rice grind. 250 g of koji mold and 3 L of water were added to the grind, which was left to stand at 55° C. for 16 hours. Subsequently, solid-liquid separation was carried out using a filter to obtain 2.6 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 3

White rice was milled in a grinder to obtain 1 kg of white rice grind. 5 g of a starch-degrading enzyme and 3 L of water were added to the grind, which was left to stand at 55° C. for 16 hours. Subsequently, solid-liquid separation was carried out using a filter to obtain 2.5 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 4

White rice was milled in a grinder to obtain 1 kg of white rice grind. 5 g of a fiber-degrading enzyme and 3 L of water were added to the grind, which was left to stand at 50° C. for 16 hours. Subsequently, solid-liquid separation was carried out using a filter to obtain 2.2 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 5

White rice was milled in a grinder to obtain 1 kg of white rice grind. 5 g of a fat-degrading enzyme and 3 L of water were added to the grind, which was left to stand at 50° C. for 16 hours. Subsequently, solid-liquid separation was carried out using a filter to obtain 2.1 L of filtrate. The filtrate was heated at 85° C. for 30 minutes arid, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 6

White rice was milled in a grinder to obtain 1 kg of white rice grind. 5 g of a liquefying enzyme and 3 L of water were added to the grind, which was left to stand at 60° C. for four hours. Subsequently, it was heated to an elevated temperature and, after cooling, 5 g of a starch-degrading enzyme were added, followed by leaving at 55° C. for four hours. Subsequently, solid-liquid separation was carried out using a filter to obtain 2.6 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 7

White rice was milled in a grinder to obtain 1 kg of white rice grind. 5 g of a liquefying enzyme and 3 L of water were added to the grind, which was left to stand at 60° C. for four hours. Subsequently, it was heated to an elevated temperature and, after cooling, 5 g of a fat-degrading enzyme were added, followed by leaving at 55° C. for four hours. Subsequently, solid-liquid separation was carried out using a filter to obtain 2.5 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 8

White rice was milled in a grinder to obtain 1 kg of white rice grind. 5 g of a liquefying enzyme and 3 L of water were added to the grind, which was left to stand at 60° C. for four hours. Subsequently, it was heated to an elevated temperature and, after cooling, 5 g of a fiber-degrading enzyme were added, followed by leaving at 55° C. for four hours. Subsequently, solid-liquid separation was carried out using a filter to obtain 2.5 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 9

White rice was milled in a grinder to obtain 1 kg of white rice grind. 3 L of 1/10 N hydrochloric acid were added to the grind, which was thoroughly stirred and left to stand for 24 hours. Subsequently, solid-liquid separation was carried out using a filter and then neutralization was carried out with caustic soda to obtain 2.3 L of a liquid extract. The extract was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 10

White rice was milled in a grinder to obtain 1 kg of white rice grind. 3 L of 95% ethanol were added to the grind, which was thoroughly stirred and left to stand for four days. Subsequently, solid-liquid separation was carried out using a filter to obtain 2 L of a liquid extract. 4 L of water were added to the filtrate and the ethanol was distilled off on a rotary evaporator to 2 L. It was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 11

White rice was milled in a grinder to obtain 1 kg of white rice grind. 5 g of a liquefying enzyme and 3 L of water were added to the grind, which was left to stand at 60° C. for four hours. Subsequently, it was heated to an elevated temperature and, after cooling, 5 g of a starch-degrading enzyme were added, followed by leaving at 55° C. for four hours. After cooling, yeast was added and fermentation was carried out for 15 days. Subsequently, solid-liquid separation was carried out using a filter to obtain 2.5 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 12

White rice was milled in a grinder to obtain 1 kg of white rice grind. 5 g of a liquefying enzyme and 3 L of water were added to the grind, which was left to stand at 60° C. for four hours. Subsequently, it was heated to an elevated temperature and, after cooling, 5 g of a starch-degrading enzyme were added, followed by leaving at 55° C. for four hours. After cooling, heat sterilization was carried out and, after cooling, lactic acid bacteria were added, followed by fermentation at 37° C. for two days. Subsequently, solid-liquid separation was carried out using a filter to obtain 2.3 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Production Example 13

White rice was milled in a grinder to obtain 1 kg of white rice grind. 5 g of a liquefying enzyme and 3 L of water were added to the grind, which was left to stand at 60° C. for four hours. Subsequently, it was heated to an elevated temperature and, after cooling, 5 g of a starch-degrading enzyme were added, followed by leaving at 55° C. for four hours. Subsequently, 150 ml of 95% ethanol and acetic acid bacteria were added and fermentation was carried out for 15 days. Subsequently, solid-liquid separation was carried out using a filter to obtain 2.4 L of filtrate. The filtrate was heated at 85° C. for 30 minutes and, after cooling, 3 ml of the filtrate were dialyzed at 4° C. for 12 hours, with 2 L of PBS buffer (pH 7.5) as the external solution, using a dialysis membrane (Spectra Biotech Membrane/Por 2.1, MWCO 8000, 00016 mm, manufactured by Spectra/Por). The dialyzed internal solution was then concentrated to the original concentration to obtain the product of this example.

Test Example 1

Osteoblast Proliferation Test

Cells used: osteoblasts (mouse Osteoblast MC3T3-E1)
Medium used: DMEM
Sample used: Production Example 12
Osteoblasts were seeded on a 12-well microplate at a concentration of 10% and preculture was carried out at 37° C. under 5% $CO_2$ until the cells were adhered. After confirming the adhesion of the cells, a sample was added to the medium to a predetermined concentration and culture was carried out at 37° C. under 5% $CO_2$. Then, the number of cells in an ocular micrometer (ocular ×10, objective ×4, 1 mm×1 mm) was counted with time using an inverted microscope. Measurements were made at three points in a well and averaged to provide a measured value. For comparison, measurements were also made on a sample before dialysis. The results are shown in FIG. 1 (before dialysis) and FIG. 2 (after dialysis). Although not specified, similar results were obtained for other Production Examples.

Test Example 2

Ethanol-Induced Damage Repair Test

Cells used: rat gastric mucosa epithelial cells (RGM1)
Medium used: (DMEM:Ham F12=1:1)+20% FBS
Sample used: Production Example 12
Gastric mucosa epithelial cells were seeded on a 12-well microplate at a concentration of 10% and preculture was carried out at 37° C. under $CO_2$ until subconfluent was reached. Using a cell scraper, part of the cells was scraped linearly and the medium was replaced with a medium having 3% ethanol and a predetermined concentration of sample added. Culture was carried out at 37° C. under 5% $CO_2$ for 60 hours and the location of the forefront cells filling the scraped part was recorded. For comparison, similar tests were made for a case where 3% ethanol was only added and a case where water was only added. The results are shown in FIG. 3. Although not specified, similar results were obtained for other Production Examples.

The invention claimed is:
1. A method of repairing damaged tissue, comprising administering to a damaged tissue, an effective amount of a white rice fraction, wherein said white rice fraction is obtained by the steps comprising:
 (a) milling white rice and adding water and a liquefying enzyme to the milled white rice;
 (b) allowing the mixture of part (a) to stand,
 (c) heating and cooling the mixture of part (b),
 (d) performing heat sterilization on the cooled mixture of part (c),
 (e) fermenting the heat-sterilized mixture of part (d) with lactic acid bacteria to create a fermented mixture,
 (f) filtering the fermented mixture of part (e) to obtain a filtrate,
 (g) dialyzing the filtrate of part (f) with an 8K dialysis membrane,
 (h) collecting the solution inside the dialysis membrane after dialysis and
 (i) concentrating the solution of part (h).

* * * * *